United States Patent [19]

Hitchcock, Jr. et al.

[11] Patent Number: 4,519,795
[45] Date of Patent: * May 28, 1985

[54] DISPOSABLE SWAB

[75] Inventors: James R. Hitchcock, Jr.; Charles J. Nevens, both of Barrington, Ill.

[73] Assignee: Baxter Travenol Laboratories, Inc., Deerfield, Ill.

[ * ] Notice: The portion of the term of this patent subsequent to Nov. 23, 1999 has been disclaimed.

[21] Appl. No.: 413,397

[22] Filed: Aug. 31, 1982

Related U.S. Application Data

[63] Continuation of Ser. No. 216,037, Dec. 15, 1980, Pat. No. 4,360,020, which is a continuation-in-part of Ser. No. 150,011, May 15, 1980, abandoned.

[51] Int. Cl.$^3$ ............................................. A61M 35/00
[52] U.S. Cl. .................................... 604/289; 401/132; 604/310
[58] Field of Search ................. 604/289, 310; 128/756, 128/759; 401/126, 130, 132, 196

[56] References Cited

U.S. PATENT DOCUMENTS

| | | |
|---|---|---|
| 2,699,779 | 1/1955 | Lustig . |
| 3,299,464 | 1/1967 | O'Brien et al. ...................... 401/132 |
| 3,369,267 | 2/1968 | Friedland et al. ................... 401/132 |
| 3,386,793 | 6/1968 | Stanton . |
| 3,527,342 | 9/1970 | Manzo . |
| 3,635,567 | 1/1972 | Richardson, Jr. . |
| 3,826,259 | 7/1974 | Bailey . |
| 3,860,348 | 1/1975 | Doyle . |
| 3,917,116 | 11/1975 | Mason . |
| 4,053,053 | 10/1977 | Tumangday . |
| 4,140,409 | 2/1979 | DeVries ............................. 401/132 |
| 4,173,978 | 11/1979 | Brown ............................... 401/132 |

Primary Examiner—C. Fred Rosenbaum
Assistant Examiner—Sherri E. Vinyard
Attorney, Agent, or Firm—Paul C. Flattery; Daniel D. Ryan

[57] ABSTRACT

A disposable swab for application of medicament and the like to the skin, which comprises a flat, sheet-like strip and a pad member centrally attached to at least one side of the strip. The first inner pair of fold lines is transversely positioned in the strip, with each fold line of the first pair being positioned on opposite sides of, and adjacent opposite ends of, the pad member by generally equal distances, to permit opposed terminal portions of the strip to be folded rearwardly relative to the pad. A second, outer pair of fold lines may be transversely positioned in the strip, each fold line of the second pair being positioned adjacent opposite ends of the strip by generally equal distances to permit end portions of the rearwardly folded terminal portions to be pinched by the fingers together into flat, abutting relation. Accordingly, the strip can form a structure which is generally triangular in cross section, with the base of the trianglar cross section carrying the pad member.

7 Claims, 7 Drawing Figures

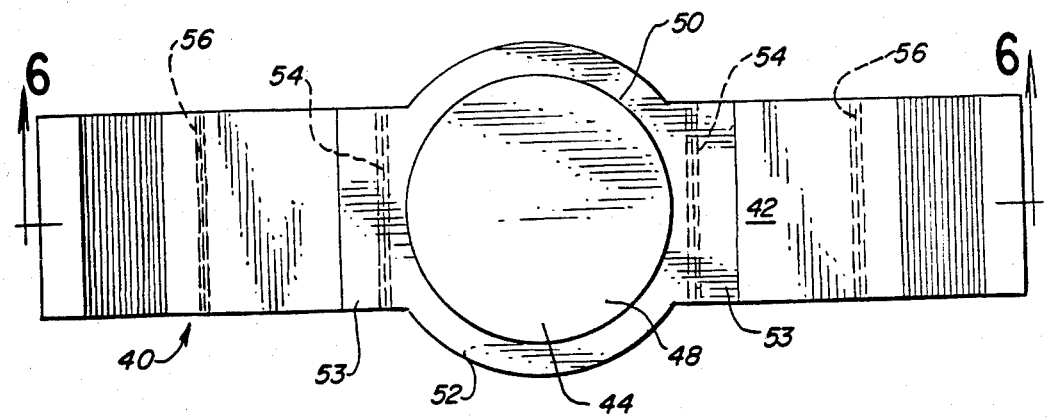
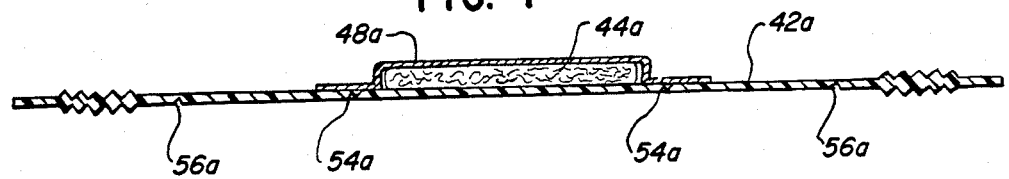
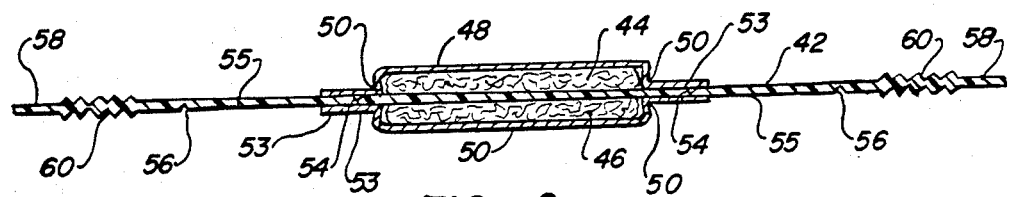

DISPOSABLE SWAB

CROSS-REFERENCE TO RELATED APPLICATION

This is a continuation of application Ser. No. 216,037, filed Dec. 15, 1980, now U.S. Pat. No. 4,360,020 which is a continuation-in-part of U.S. application Ser. No. 150,011, filed May 15, 1980 now abandoned.

TECHNICAL FIELD

This application relates to an inexpensive, disposable swab member for the application of medicament to the skin. Preferably, the disposable swab member as provided to the user carries the medicament in sealed, sterile manner so that the user has only to grasp the swab in the manner specified herein, and to open a frangible pouch, exposing the medicament which is carried by a pad member on the swab.

Particularly, it is, of course, necessary to sterilize the skin prior to making a venous puncture or other hypodermic needle injection. The swab of this invention, which is of very low cost, can provide a premeasured amount of sterilizing agent impregnated in its pad for application to the skin prior to making such a venous puncture. This provides particular convenience and advantage, in that the individual dosages of antiseptic are ready for application, avoiding the need for wetting a sponge or swab with the appropriate antiseptic.

Furthermore, the swab of this invention may be provided in a flat configuration, so that it may be advantageously included in prepackaged medical procedure trays, intravenous solution administration sets, blood bag packages, and other devices, so that the user does not have to look for the antiseptic or to prepare a conventional swab, or do anything other than fold the swab of this invention and remove the frangible pouch in order to properly apply the medicament (or cosmetic, etc.).

The disposable swab of this invention may be used for the application of any desired medicament, such as cortisone ointment or the like. Likewise, the swab of this invention may be used for the application of cosmetic ointments, make up, rouge, hair dye or any other material as may be desired, particularly where it is convenient for a prepackaged single dose of the material to be applied at a minimum of cost, and for very substantial convenience both in packaging and in use. For example, the swab may be used to add "touch up" stain to furniture, or similar uses. The swab may also be used in dry form to pick up materials from another container for application to the skin or another surface.

BACKGROUND ART

While other disposable swabs have been produced, for example as shown in U.S. Pat. No. 4,140,409, the swab of this invention is unsurpassed in simplicity, low cost, and economy, permitting effective mass production and widespread use thereof.

Similarly, U.S. Pat. No. 3,369,267, which discloses a combination container and applicator having a pad, is of substantially more complex structure and of greater manufacturing cost than the disposable swab of this invention.

DISCLOSURE OF INVENTION

In this invention, a disposable swab is provided, typically for application of medicament and the like to the skin. The swab comprises a flat, sheet-like stiff strip, plus a pad member centrally attached to at least one side of the strip.

A first, inner pair of fold lines is transversely positioned in the strip, each fold line of the inner pair being positioned on opposite sides of and adjacent an opposite end of the pad member by generally equal distances. The effect of this is to permit opposed, terminal portions of the strip to be folded rearwardly relative to the pad.

A second, outer pair of fold lines may optionally be transversely positioned in the strip with each fold line of the outer pair being positioned adjacent opposite ends of the strip and spaced by generally equal distances to permit end portions of the rearwardly folded terminal portions of the strip, to be pinched by the fingers together into flat, abutting relation.

Accordingly, the folded strip forms a structure which is generally triangular in cross section, the base of the triangular cross section carrying the pad member.

Preferably, the pad member, which may preferably be made of an absorbent, sponge-like material of any suitable type, carries the medicament preferably in spongy interstices of the pad, so that it can be expressed out onto the skin or other surface as the swab is utilized.

Separate pad members may be carried on opposite sides of the strip. In use, the strip is first folded rearwardly relative to one pad to use it, and then refolded rearwardly relative to the opposite pad, to use it.

It is also preferable for each pad member to be enclosed in a frangible pouch which is sealed at its edges to the strip.

The flat, sheet-like strip may be of generally stiff cardboard, typically with an aluminum foil laminate on one side, a commercially available material. The pouch may also comprise conventional aluminum foil with a thin thermoplastic layer laminated to it, so that the frangible foil pouch may be heat-sealed at its edges to the foil side of the cardboard strip, thus enclosing the pad member. Also, the generally stiff strip may be made of a flexible plastic such as polyethylene, polypropylene, or the like. In this case, the fold lines may be of living hinge construction.

The pad member may be made of conventional polyester or similar sponge material if desired, and may be attached to the preferably cardboard or plastic strip on the aluminun foil-laminated side by means of a conventional adhesive, a heat seal, or any other desired technique.

The medicament carried by the pad member may specifically be soap, or an antiseptic such as the well-known PVP Iodine, which is a commercially available antiseptic, or any other desired antiseptic or other medicament, cosmetic, or other material. It is a particular advantage of the use of an antiseptic that no sterilization of the swab pad member is required.

As stated above, the swab may be advantageously stored and packaged in its flat configuration. Then when it is to be used, the inner pair of fold lines are folded, to swing the terminal portions of the strip rearwardly, while the outer pair of fold lines are folded so that the end portions of the rearwardly folded terminal portions may be pinched by the fingers together in a flat, abutting relation. The frangible pouch may then be removed from about the pad member, and the swab is available for use.

Alternatively, the swab may be folded, and the end portions may be glued together so that the swab occupies its triangular configuration during storage, if desired.

In the drawings,

FIG. 5 is a plan view of another embodiment of the swab of this invention.

FIG. 6 is an elevational view, taken partly in section, of the swab of FIG. 5.

FIG. 7 is an elevational view of another embodiment of the swab of this invention similar in its plan view aspect to that of FIG. 5.

Figure 1:
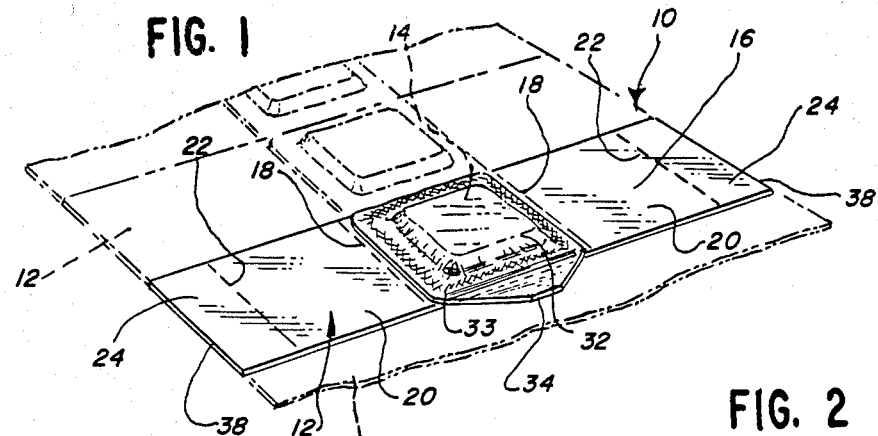
FIG. 1 is a perspective view of the swab of this invention in its flat form, shown as part of a strip of swabs.
Figure 2:
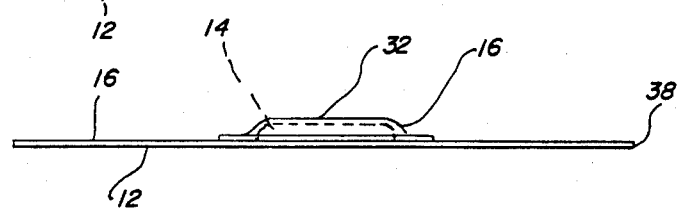
FIG. 2 is an elevational view of the swab of FIG. 1.

Referring to the drawings, the disposable swab 10 of this invention comprises flat sheet-like strip 12, which may be a cardboard strip laminated on the pad-facing side 16 with aluminum foil, as previously described. Pad member 14 may comprise polyester sponge material or any other absorbent pad-like material as may be desired for use, secured by adhesive or heat sealing to the foil face 16 of flat, sheet-like strip 12. Pad member 14 may be impregnated with a medicament and the like.

Figure 3:
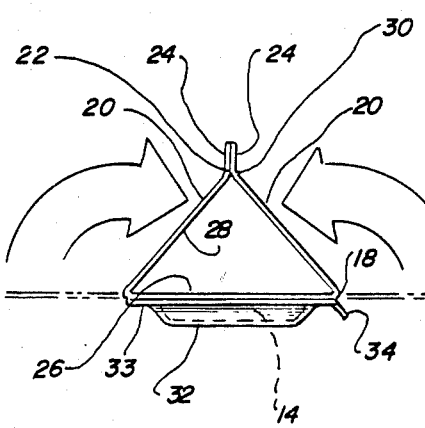
FIG. 3 is an elevational view of the swab of FIG. 2 in inverted position and folded into its position of use.
Figure 4:
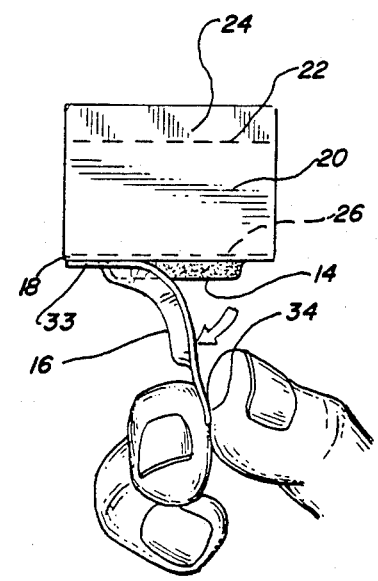
FIG. 4 is an elevational view similar to FIG. 3, but rotated by 90°, showing the removal of the frangible pouch for use of the swab.

Strip 12 may be mechanically scored in conventional manner to define inner and outer pairs of fold lines. The inner pair of fold lines 18 are positioned on opposite sides of pad 14 and positioned adjacent the opposite ends of pad 14 by generally equal distances, as shown in FIG. 1, to permit opposed terminal portions 20 of strip 12 to be folded rearwardly relative to pad 4, as shown in FIGS. 3 and 4.

The outer pair of fold lines 22 are also provided, being positioned adjacent opposite ends of strip 12 by generally equal distance. Fold lines 22 define end portions 24 of terminal portions 20, which may be pinched by the fingers together into flat, abutting relation as shown in FIGS. 3 and 4 to serve as a finger-grippable handle portion, for holding the disposable swab during the swabbing process.

Accordingly, as can be seen, strip 12 can be folded into a structure which is generally triangular in cross section, with base panel 26 of the triangular cross section carrying pad member 14. The inner portions 28 of terminal portions 20 define a pair of triangular leg panels which can fold together about fold lines 18 to define an apex 30, where outer fold lines 22 are located.

Pad member 14 is enclosed in a frangible pouch 32 which may be made of aluminum foil laminated to a thin plastic layer of polyethylene or the like, and then preferably heat sealed using said plastic layer at its edges 33 to strip 12, to completely enclose pad 14. A conventional tear tab 34 may be provided for easy manual tearing removal of frangible pouch 32 for exposure of pad 14. Thereafter, swab 10 may be used, transferring the medicament stored in pad 14 to the skin. The swab may then be disposed of.

The swab of this invention is an extremely low cost item, which has the added advantage that it may be stored in flat form until its use is desired. It is easily folded together for use and opened, and presents little disposal problem. Also, swabs 10 may be mass produced as a strip of swabs 12 as shown in FIG. 1, joined together at their sides by lines of tearing weakness 38 so that individual swabs may be torn off the strip for use.

Thus the swabs of this invention can be sold as a coiled roll of swabs, for example, in a dispenser box, for ease of storage. Also, the strips of swabs may be made from rolls of raw materials by automated manufacturing equipment.

Referring to FIGS. 5 and 6, another embodiment of swab 40 is disclosed. A strip of semi-stiff polyethylene sheeting 42 carries a pair of circular pad members 44, 46 on respective sides of plastic strip 42, being solvent, adhesive, or heat-sealed to the strip as may be desired.

Covering each pad 44, 46 is a frangible pouch 48, 50 which may be of conventional design, each sealed with a peripheral seal line 50, and each defining an annular, unsealed flange portion 52 with gripping tabs 53. Each frangible pouch 48, 50 may be plastic laminated foil as in the previous embodiment.

Inner pair of fold lines 54 may be formed by impressing a groove as shown in FIG. 6 into plastic strip 42. Accordingly, as fold lines 54 are folded in the manner of this invention to expose one or the other of pads 44, 46, they can form a living hinge in the known manner of thermoplastics such as polyethylene, to form an easily foldable joint, so that the opposed terminal portions 55 of strip 42 may be folded rearwardly, relative to one or the other of pads 44, 46, into a triangular configuration analogous to that of the previous embodiment.

Furthermore, outer fold lines 56 of similar design to lines 54 may be provided for a function analogous to outer fold lines 22 of the previous embodiment, to permit end portions 58 to serve as a handle member in a manner similar to the previous embodiment. Since strip 42 is made of plastic, serrations or ridges 40 may be molded or pressed into the plastic strip in the outer end portion 58, to further facilitate manual gripping of the structure and to avoid slippage of the swab in the fingers as it is being used.

Accordingly, in one specific embodiment of use as shown in FIGS. 5 and 6, pad 44 may be impregnated with a surgical soap, while pad 46 may be impregnated with an antiseptic such as PVP Iodine. This structure may be placed into a "prep" kit, and serves the function of two swabs instead of one.

First, frangible pouch 48 may be removed by folding portions 54 rearwardly about fold lines 54 relative to swab 44 into a triangular configuration for gripping, which tends to expose tab portion 53 of pouch 48. Tab portion 53 is grasped and ripped away, to remove pouch 48 and expose the pad member 44 and the soap which it carries. The soap is applied to skin of the patient in conventional manner, to cleanse an area.

Following this, for application of the PVP Iodine antiseptic in pad 56, opposed terminal portions 54 of the strip are then folded back in the opposite direction, rearwardly relative to pad 56, into another triangular configuration, with end portions 58 being gripped by the fingers. The tab portion 53 of frangible pouch 50 is then exposed for easy gripping, and it also may be ripped away by the fingers, removing pouch 50, exposing pad 56 with its antiseptic for application.

Accordingly, an extremely inexpensive applicator or swab is provided in which, if desired, two different pads having two different materials for application are provided by the same device, which may be sequentially applied with great convenience at extremely low cost.

As stated above, there is no particular limitation of the type of materials which may be applied by the swab of this invention, or impregnated into the one or more pads carried by the device.

Referring to FIG. 7, another embodiment is disclosed, including a similar strip 42a, which may be of identical design to strip 42. Basically, the embodiment of FIG. 7 may be identical to the embodiment of FIG. 6, except that one of the pads is omitted. Pad 44a may be identical to pad 44, while frangible pouch 48a may be identical to pouch 48. The various fold lines 54a and 56a are also of identical function to the prior analogous fold lines.

The above has been offered for illustrative purposes only, and it not intended to limit the scope of the invention of this application, which is as defined in the claims below.

That which is claimed is:

1. A disposable swab comprising
   a flat, generally stiff strip,
   a pad member centrally attached to at least one side of said strip,
   means defining an inner pair of fold lines extending in said strip on opposite sides of said pad member by generally equal distances for permitting opposed, terminal portions of said strip to be folded rearwardly relative to said pad to form a structure of generally triangular cross section which can be grasped by the fingers, the base of said triangular cross section carrying said pad member, and
   a removable pouch sealingly enclosing said pad member and including
      a main body portion sealed to said strip along a line which extends between said opposite pad member sides and each of said inner pair of fold lines and remaining sealed to said strip along said line when said strip is folded rearwardly about said inner pair of fold lines to form said triangular cross section structure, and
      a tab portion extending outwardly from said main body portion and beyond one of said inner pair of fold lines in an unsecured relationship with said strip, said tab portion being exposed for manual gripping by the attendant when said strip is folded rearwardly about said one inner fold line to facilitate removal of said sealed main body portion of said pouch from said strip after said strip has been folded rearwardly about said one inner fold line.

2. A disposable swab comprising
   a flat, generally stiff strip,
   a pad member centrally attached to at least one side of said strip,
   first means defining an inner pair of fold lines extending in said strip on opposite sides of said pad member by generally equal distances for permitting opposed, terminal portions of said strip to be folded rearwardly relative to said pad,
   second means defining an outer pair of fold lines extending in said strip on opposite ends of said strip and spaced by generally equal distances from said inner pair of fold lines for permitting end portions of said rearwardly folded terminal portions to be pinched by the fingers together into flat, abutting relation, whereby said strip can form a structure which is generally triangular in cross section, the base of said triangular cross section carrying said pad members, and
   a removable pouch sealingly enclosing each of said pad members and including
      a main body portion sealed to said strip along a line which extends between said opposite pad member sides and each of said inner pair of fold lines, and
      a tab portion extending outwardly from said main body portion and beyond one of said inner pair of fold lines in an unsecured relationship with said strip, said tab portion being exposed for manual gripping by the attendant when said strip is folded rearwardly about said one inner fold line to facilitate removal of said sealed main body portion of said pouch from said strip.

3. The disposable swab of claim 1 or 2 wherein said stiff strip comprises a thermoplastic sheet.

4. The disposable swab of claim 1 or 2 wherein each side of said strip carries one of said pad members which is enclosed by said removable pouch.

5. A plurality of disposable swabs joined together into a strip of separable swabs, comprising
   a flat, generally stiff strip,
   a plurality of spaced pad members centrally attached to at least one side of said strip,
   means defining a first pair of fold lines extending in said strip on opposite sides of each of said pad members by generally equal distances,
   means defining lines of tearing weakness extending in said strip transversely of said fold lines for separating said strip into individual, flattened swabs, each of said swabs carrying at least one of said pad members and said associated first pair of fold lines permitting each of said swabs, when separated, to be folded rearwardly relative to said associated pad member to form a structure of generally triangular cross section which can be grasped by the fingers, the base of said triangular cross section carrying said associated pad member, and
   a removable pouch sealingly enclosing each of said pad members and including
      a main body portion sealed to said strip along a line which extends between said opposite pad member sides and each of said first pair of fold lines and remaining sealed to said strip along said line as said associated swab, when separated, is folded rearwardly about said pair of fold lines to form said triangular cross section structure, and
      a tab portion extending outwardly from said main body portion and beyond one of said fold lines in an unsecured relationship with said strip to facilitate removal of said sealed main body portion from said associated swab after said swab, when separated, has been folded rearwardly about said one fold line.

6. The strip of separable swabs of claim 5 wherein said sheet-like strip comprises a thermoplastic sheet.

7. The strip of separable swabs of claim 5 and further including means defining a second pair of fold lines positioned in said strip axially of said first pair and more remotely from each pad member on each side thereof than said first pair of fold lines.

* * * * *